(12) United States Patent
Mitkidis et al.

(10) Patent No.: US 11,078,134 B2
(45) Date of Patent: Aug. 3, 2021

(54) GAS CLEAN-UP FOR ALKANE OXIDATIVE DEHYDROGENATION EFFLUENT

(71) Applicant: SHELL OIL COMPANY, Houston, TX (US)

(72) Inventors: Georgios Mitkidis, Amsterdam (NL); Guus Van Rossum, Amsterdam (NL); Maria San Roman Macia, Amsterdam (NL); Ronald Jan Schoonebeek, Amsterdam (NL); Michael Johannes Franciscus Maria Verhaak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/486,535

(22) PCT Filed: Feb. 20, 2018

(86) PCT No.: PCT/EP2018/054084
§ 371 (c)(1),
(2) Date: Aug. 16, 2019

(87) PCT Pub. No.: WO2018/153831
PCT Pub. Date: Aug. 30, 2018

(65) Prior Publication Data
US 2020/0002251 A1    Jan. 2, 2020

(30) Foreign Application Priority Data
Feb. 22, 2017  (EP) .................................. 17386007
Feb. 22, 2017  (EP) .................................. 17386008

(51) Int. Cl.
*C07C 5/48*    (2006.01)
*B01J 23/00*   (2006.01)
(Continued)

(52) U.S. Cl.
CPC ............... *C07C 5/48* (2013.01); *B01J 23/002* (2013.01); *B01J 23/80* (2013.01); *B01J 35/0026* (2013.01);
(Continued)

(58) Field of Classification Search
CPC ....... C07C 5/333; C07C 5/48; C07C 2523/06; C07C 2523/72; C07C 2523/80;
(Continued)

(56) References Cited

U.S. PATENT DOCUMENTS 4,299,800 A   11/1981  Nishikawa et al.
4,956,330 A    9/1990  Elliott et al.
(Continued)

FOREIGN PATENT DOCUMENTS

DE    102005000798 A1   7/2006
EP         0306945 A1   3/1989
(Continued)

OTHER PUBLICATIONS

International Search Report and Written Opinion received for PCT Patent Application No. PCT/EP2018/054084 dated Apr. 26, 2018, 09 pages.

*Primary Examiner* — Youngsul Jeong
*Assistant Examiner* — Jason Y Chong (57) ABSTRACT

The invention relates to a process for the production of an alkene by alkane oxidative dehydrogenation, comprising: (a) subjecting a stream comprising an alkane to oxidative dehydrogenation conditions, comprising contacting the alkane with oxygen in the presence of a catalyst comprising a mixed metal oxide, resulting in a stream comprising alkene, unconverted alkane, water, carbon dioxide, unconverted oxygen, carbon monoxide and optionally an alkyne; (b) removing water from at least part of the stream comprising alkene,
(Continued)

unconverted alkane, water, carbon dioxide, unconverted oxygen, carbon monoxide and optionally an alkyne resulting from step (a), resulting in a stream comprising alkene, unconverted alkane, carbon dioxide, unconverted oxygen, carbon monoxide and optionally alkyne; (c) removing unconverted oxygen, carbon monoxide and optionally alkyne from at least part of the stream comprising alkene, unconverted alkane, carbon dioxide, unconverted oxygen, carbon monoxide and optionally alkyne resulting from step (b), wherein carbon monoxide and optionally alkyne are oxidized into carbon dioxide, resulting in a stream comprising alkene, unconverted alkane and carbon dioxide; (d) optionally removing carbon dioxide from at least part of the stream comprising alkene, unconverted alkane in and carbon dioxide resulting from step (c), resulting in a stream comprising alkene and unconverted alkane; (e) optionally separating at least part of the stream comprising alkene and unconverted alkane resulting from step (d), into a stream comprising alkene and a stream comprising unconverted alkane; (f) optionally recycling unconverted alkane from at least part of the stream comprising unconverted alkane resulting from step (e), to step (a).

8 Claims, 1 Drawing Sheet (51) Int. Cl.
  *B01J 23/80* (2006.01)
  *B01J 35/00* (2006.01)
  *B01J 35/02* (2006.01)
(52) U.S. Cl.
  CPC .......... *B01J 35/026* (2013.01); *B01J 2523/17* (2013.01); *B01J 2523/27* (2013.01); *B01J 2523/31* (2013.01); *C07C 2521/04* (2013.01); *C07C 2523/06* (2013.01); *C07C 2523/72* (2013.01); *C07C 2523/80* (2013.01)
(58) Field of Classification Search
  CPC . C07C 2521/04; B01J 35/0026; B01J 35/026; B01J 23/002; B01J 23/80; B01J 2523/17; B01J 2523/27; B01J 2523/31
  See application file for complete search history.

(56) References Cited

U.S. PATENT DOCUMENTS

| | | | |
|---|---|---|---|
| 5,157,204 A † | 10/1992 | Brown | |
| 5,446,232 A | 8/1995 | Chen et al. | |
| 6,747,066 B2 | 6/2004 | Wang et al. | |
| 7,091,377 B2 | 8/2006 | Borgmeier et al. | |
| 2004/0147393 A1 | 7/2004 | Hibst et al. | |
| 2008/0221374 A1* | 9/2008 | Crone | C07C 7/11 585/252 |
| 2010/0256432 A1* | 10/2010 | Arnold | C07C 5/48 585/655 |
| 2014/0249339 A1* | 9/2014 | Simanzhenkov | B01J 23/002 585/252 |
| 2016/0326070 A1 | 11/2016 | Winkler et al. | |

FOREIGN PATENT DOCUMENTS

| | | |
|---|---|---|
| EP | 0421169 A1 | 4/1991 |
| EP | 0499402 A1 | 8/1992 |
| WO | 0190043 A1 | 11/2001 |
| WO | 0224614 A1 | 3/2002 |
| WO | 03055838 A1 | 7/2003 |
| WO | 03064035 A1 | 8/2003 |
| WO | 2010096909 A1 | 9/2010 |
| WO | 2010115108 A1 | 10/2010 |
| WO | 2012101069 A1 | 8/2012 |

\* cited by examiner
† cited by third party

GAS CLEAN-UP FOR ALKANE OXIDATIVE DEHYDROGENATION EFFLUENT

CROSS REFERENCE TO RELATED APPLICATIONS

This is a national stage application of International Application No. PCT/EP2018/054084, filed 20 Feb. 2018, which claims benefit of priority to European Patent Application Nos. 17386008.1, filed 22 Feb. 2017 and 17386007.3, filed 22 Feb. 2017.

FIELD OF THE INVENTION

The present invention relates to a process for the production of an alkene by alkane oxidative dehydrogenation (oxydehydrogenation; ODH) which comprises a step of removing unconverted oxygen, carbon monoxide and optionally alkyne from alkane ODH effluent.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts.

In particular, in said alkane ODH process oxygen may be used as the oxidizing agent. In addition to alkene and unconverted alkane, alkane ODH effluent may comprise unconverted oxygen. Generally, in order to avoid the risk of operating the alkane ODH process at oxygen depletion conditions, more oxygen is fed than required in which case the alkane ODH effluent comprises unconverted oxygen. Further, in some cases, an additional amount of oxygen may have to be added temporarily after some time, in order to increase a reduced catalyst activity. Thus, generally, the possibility of using a relatively high amount of oxygen in the alkane ODH process advantageously provides flexibility on ODH reactor operation at desired conditions. The less desired alternative would be to feed less oxygen and/or to fully convert the oxygen in the ODH reactor. However, on the other hand, having unconverted oxygen in the ODH effluent increases the risk of explosion hazards because of the presence of hydrocarbons (alkanes; alkenes) in combination with a relatively high oxygen concentration in the back-end separation section, in which section distillation may be applied to achieve the desired separations. In addition, such unconverted oxygen may be involved in some undesired trace chemistry, for example resulting in peroxides which as such could also result in an unwanted risk of explosion hazards.

In view of the above, it is desired to remove unconverted oxygen from ODH effluent before the latter effluent enters the above-mentioned back-end separation section.

Apart from unconverted oxygen, ODH effluent may comprise carbon monoxide. Carbon monoxide may cause problems in downstream conversion processes. For example, carbon monoxide may be a poison to a catalyst used in such further downstream conversion process resulting in a reduced catalyst activity. An example of such downstream conversion process is a process wherein the alkene product of the alkane ODH process is further converted. Further, there may not be sufficient capacity for the removal of carbon monoxide and any other light components, for example by distillation, in the back-end separation section which is also downstream of the alkane ODH step. Still further, there may not be sufficient capacity for converting carbon monoxide and water into methane in any downstream methanation reactor.

Therefore, in view of the above, it may also be desired to remove carbon monoxide from ODH effluent before the latter effluent enters the above-mentioned back-end separation section.

Apart from unconverted oxygen and carbon monoxide, ODH effluent may comprise an alkyne. Such alkyne may be produced by a further oxidative dehydrogenation of the desired alkene. For example, acetylene may be produced from ethylene in such way. Alkynes, such as acetylene, may cause problems in downstream conversion processes. For example, they may be a poison to a catalyst used in such further downstream conversion process resulting in a reduced catalyst activity. An example of such downstream conversion process is a process wherein the alkene product of the alkane ODH process is further converted. Further, there may not be sufficient capacity for the removal of alkynes, for example by distillation or hydrogenation, in the back-end separation section which is also downstream of the alkane ODH step. It is costly to separate for example acetylene from ethylene, usually by extractive distillation and/or selective hydrogenation to the corresponding alkene, for example acetylene to ethylene.

Therefore, in view of the above, it may also be desired to remove alkynes, such as acetylene, from ODH effluent before the latter effluent enters the above-mentioned back-end separation section.

WO2010115108 discloses a process for the oxidative dehydrogenation of ethane to ethylene, comprising: contacting an ethane feed and an oxygen-containing gas in the presence of an oxidative dehydrogenation catalyst in an oxidative dehydrogenation reaction zone under conditions to oxidatively dehydrogenate at least a portion of the ethane to produce a product stream comprising ethylene, carbon oxides, water, and unreacted oxygen and ethane, wherein an oxygen concentration in the product stream is at least 0.1 mol %; contacting the product stream with an oxygen elimination catalyst in an oxygen elimination reaction zone to combust at least a portion of the oxygen; recovering from the oxygen elimination reaction zone an effluent having a reduced oxygen content; separating water from the effluent; separating carbon oxides and any non-condensable gas(es) from the ethylene and the unreacted ethane; and separating the ethylene from the unreacted ethane.

In the process of above-mentioned WO2010115108, oxygen removal (oxygen elimination) takes place before water removal (water separation). Further, according to said WO2010115108, an oxidation catalyst may be used to have the oxygen in the ethane ODH reactor effluent combust carbon monoxide. In the latter case, oxygen and carbon monoxide are converted into carbon dioxide, thereby resulting in simultaneously removing both oxygen and carbon monoxide.

Still further, according to said WO2010115108, another type of oxygen elimination reactor may incorporate addition of $H_2$ and a hydrogenation catalyst to hydrogenate the oxygen (rather than oxidation catalyst to accomplish combustion). According to said WO2010115108, such a system may have the additional benefit of hydrogenating various by-products to the extent that some may be present, such as acetylene and oxygenates. In the latter case, oxygen and the alkyne (for example acetylene) are hydrogenated by adding hydrogen gas ($H_2$) as hydrogenating agent, thereby resulting in simultaneously removing both oxygen and the alkyne. However, it is generally considered cumbersome to introduce another chemical (in this case: $H_2$ hydrogenating agent) into the process in order to convert a contaminant. In addition, the use of $H_2$ may be hazardous, especially when combined with oxygen. In particular, hydrogen ($H_2$) is more reactive than acetylene in reacting with oxygen. Further, generally, such introduction may result in other separation issues, for example separating the water as produced. Still further, it may be cumbersome to control undesired hydrogenation of the desired alkene product into the starting alkane.

It may be an object to provide a process which comprises a step of removing unconverted oxygen, carbon monoxide and optionally alkyne (for example acetylene) from effluent as produced in an alkane ODH step, by means of conversion, wherein in such oxygen and carbon monoxide removal step conversion of the alkene product and/or unconverted alkane is prevented as much as possible. Further, it may be an object to provide such process wherein oxygen, carbon monoxide and optionally alkyne are removed from alkane ODH effluent, which is technically advantageous, efficient and affordable. Such technically advantageous process would preferably result in a lower energy demand and/or lower capital expenditure.

SUMMARY OF THE INVENTION

It was found that one or more of the above-mentioned objects may be achieved in a process wherein after removal of water from an alkane oxidative dehydrogenation (ODH) effluent comprising alkene, unconverted alkane, water, carbon dioxide, unconverted oxygen, carbon monoxide and optionally an alkyne, unconverted oxygen, carbon monoxide and optionally alkyne are removed from that stream, wherein carbon monoxide and optionally alkyne are oxidized into carbon dioxide, resulting in a stream comprising alkene, unconverted alkane and carbon dioxide.

Accordingly, the present invention relates to a process for the production of an alkene by alkane oxidative dehydrogenation, comprising:

(a) subjecting a stream comprising an alkane to oxidative dehydrogenation conditions, comprising contacting the alkane with oxygen in the presence of a catalyst comprising a mixed metal oxide, resulting in a stream comprising alkene, unconverted alkane, water, carbon dioxide, unconverted oxygen, carbon monoxide and optionally an alkyne;

(b) removing water from at least part of the stream comprising alkene, unconverted alkane, water, carbon dioxide, unconverted oxygen, carbon monoxide and optionally an alkyne resulting from step (a), resulting in a stream comprising alkene, unconverted alkane, carbon dioxide, unconverted oxygen, carbon monoxide and optionally alkyne;

(c) removing unconverted oxygen, carbon monoxide and optionally alkyne from at least part of the stream comprising alkene, unconverted alkane, carbon dioxide, unconverted oxygen, carbon monoxide and optionally alkyne resulting from step (b), wherein carbon monoxide and optionally alkyne are oxidized into carbon dioxide, resulting in a stream comprising alkene, unconverted alkane and carbon dioxide;

(d) optionally removing carbon dioxide from at least part of the stream comprising alkene, unconverted alkane and carbon dioxide resulting from step (c), resulting in a stream comprising alkene and unconverted alkane;

(e) optionally separating at least part of the stream comprising alkene and unconverted alkane resulting from step (d), into a stream comprising alkene and a stream comprising unconverted alkane;

(f) optionally recycling unconverted alkane from at least part of the stream comprising unconverted alkane resulting from step (e), to step (a).

DETAILED DESCRIPTION OF THE INVENTION

The process of the present invention comprises steps (a), (b) and (c) and optional steps (d), (e) and (f). Said process may comprise one or more intermediate steps between steps (a) and (b), between steps (b) and (c), between steps (c) and (d), between steps (d) and (e), and between steps (e) and (f). Further, said process may comprise one or more additional steps preceding step (a) and/or following step (f).

While the process of the present invention and the stream or streams used in said process are described in terms of "comprising", "containing" or "including" one or more various described steps or components, they can also "consist essentially of" or "consist of" said one or more various described steps or components.

In the context of the present invention, in a case where a stream comprises two or more components, these components are to be selected in an overall amount not to exceed 100 vol. % or 100 wt. %.

Within the present specification, "substantially no" means that no detectable amount of the component in question is present.

The present process for the production of an alkene by alkane oxidative dehydrogenation may comprise:

(a) subjecting a stream comprising an alkane to oxidative dehydrogenation conditions, comprising contacting the alkane with oxygen in the presence of a catalyst comprising a mixed metal oxide, resulting in a stream comprising alkene, unconverted alkane, water, carbon dioxide, unconverted oxygen, carbon monoxide and optionally an alkyne;

(b) removing water from a stream comprising alkene, unconverted alkane, water, carbon dioxide, unconverted oxygen, carbon monoxide and optionally an alkyne, preferably the stream resulting from step (a), resulting in a stream comprising alkene, unconverted alkane, carbon dioxide, unconverted oxygen, carbon monoxide and optionally alkyne;

(c) removing unconverted oxygen, carbon monoxide and optionally alkyne from a stream comprising alkene, unconverted alkane, carbon dioxide, unconverted oxygen, carbon monoxide and optionally alkyne, preferably the stream resulting from step (b), wherein carbon monoxide and optionally alkyne are oxidized into carbon dioxide, resulting in a stream comprising alkene, unconverted alkane and carbon dioxide;

(d) optionally removing carbon dioxide from a stream comprising alkene, unconverted alkane and carbon dioxide, preferably the stream resulting from step (c), resulting in a stream comprising alkene and unconverted alkane;

(e) optionally separating a stream comprising alkene and unconverted alkane, preferably the stream resulting from step (d), into a stream comprising alkene and a stream comprising unconverted alkane;

(f) optionally recycling unconverted alkane from a stream comprising unconverted alkane, preferably the stream comprising unconverted alkane resulting from step (e), to step (a).

Step (a) of the process of the present invention comprises subjecting a stream comprising an alkane to oxidative dehydrogenation (ODH) conditions, comprising contacting the alkane with oxygen ($O_2$) in the presence of a catalyst comprising a mixed metal oxide, resulting in a stream comprising alkene, unconverted alkane, water, carbon dioxide, unconverted oxygen, carbon monoxide and optionally an alkyne.

In alkane ODH step (a), the alkane may be an alkane containing 2 to 6 carbon atoms, which alkane is preferably a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

The product of alkane ODH step (a) may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The stream resulting from alkane ODH step (a) may comprise an alkyne. Such alkyne is the dehydrogenated equivalent of the desired alkene product. For example, in the case of ethane ODH, such alkyne may comprise acetylene (ethyne). In the case of propane ODH, such alkyne may comprise propyne (methyl acetylene).

In alkane ODH step (a), the alkane and oxygen ($O_2$) may be fed to a reactor. Said components may be fed to the reactor together or separately. That is to say, one or more feed streams, suitably gas streams, comprising one or more of said 2 components may be fed to the reactor. For example, one feed stream comprising oxygen and the alkane may be fed to the reactor. Alternatively, two or more feed streams, suitably gas streams, may be fed to the reactor, which feed streams may form a combined stream inside the reactor. For example, one feed stream comprising oxygen and another feed stream comprising the alkane may be fed to the reactor separately.

In alkane ODH step (a), the alkane and oxygen are suitably fed to a reactor in the gas phase.

Preferably, in alkane ODH step (a), that is to say during contacting the alkane with oxygen in the presence of a catalyst, the temperature is of from 300 to 500° C. More preferably, said temperature is of from 310 to 450° C., more preferably of from 320 to 420° C., most preferably of from 330 to 420° C.

Still further, in alkane ODH step (a), that is to say during contacting the alkane with oxygen in the presence of a catalyst, typical pressures are 0.1-30 or 0.1-20 bara (i.e. "bar absolute"). Further, preferably, said pressure is of from 0.1 to 15 bara, more preferably of from 1 to 8 bara, most preferably of from 3 to 8 bara.

In addition to oxygen and the alkane, an inert gas may also be fed. Said inert gas may be selected from the group consisting of the noble gases and nitrogen ($N_2$). Preferably, the inert gas is nitrogen or argon, more preferably nitrogen.

Said oxygen is an oxidizing agent, thereby resulting in oxidative dehydrogenation of the alkane. Said oxygen may originate from any source, such as for example air. Ranges for the molar ratio of oxygen to the alkane which are suitable, are of from 0.01 to 1, more suitably 0.05 to 0.5. Said ratio of oxygen to the alkane is the ratio before oxygen and the alkane are contacted with the catalyst. In other words, said ratio of oxygen to the alkane is the ratio of oxygen as fed to the alkane as fed. Obviously, after contact with the catalyst, at least part of the oxygen and alkane gets consumed.

In step (a), the alkane ODH catalyst is a catalyst comprising a mixed metal oxide. Preferably, the ODH catalyst is a heterogeneous catalyst. Further, preferably, the ODH catalyst is a mixed metal oxide catalyst containing molybdenum, vanadium, niobium and optionally tellurium as the metals, which catalyst may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for 0) is a number which is determined by the valency and frequency of elements other than oxygen.

The amount of the catalyst in alkane ODH step (a) is not essential. Preferably, a catalytically effective amount of the catalyst is used, that is to say an amount sufficient to promote the alkane oxydehydrogenation reaction.

The ODH reactor that may be used in alkane ODH step (a) may be any reactor, including fixed-bed and fluidized-bed reactors. Suitably, the reactor is a fixed-bed reactor.

Examples of oxydehydrogenation processes, including catalysts and process conditions, are for example disclosed in above-mentioned U.S. Pat. No. 7,091,377, WO2003064035, US20040147393, WO2010096909 and US20100256432, the disclosures of which are herein incorporated by reference.

In alkane ODH step (a), water is formed which ends up in the product stream in addition to the desired alkene product. Further, said product stream comprises unconverted alkane, carbon dioxide, unconverted oxygen, carbon monoxide and optionally an alkyne. That is to say, alkane ODH step (a) results in a stream comprising alkene, unconverted alkane, water, carbon dioxide, unconverted oxygen, carbon monoxide and optionally an alkyne.

Step (b) of the process of the present invention comprises removing water from a stream comprising alkene, unconverted alkane, water, carbon dioxide, unconverted oxygen, carbon monoxide and optionally an alkyne, preferably the stream resulting from step (a), in particular from at least part of the stream comprising alkene, unconverted alkane, water, carbon dioxide, unconverted oxygen, carbon monoxide and optionally an alkyne resulting from step (a), resulting in a stream comprising alkene, unconverted alkane, carbon dioxide, unconverted oxygen, carbon monoxide and optionally alkyne.

In water removal step (b), water is suitably removed by condensation. Water in the stream comprising alkene, unconverted alkane, water, carbon dioxide, unconverted oxygen, carbon monoxide and optionally an alkyne may be condensed by cooling down the latter stream to a lower temperature, for example room temperature, after which the condensed water can be separated, resulting in a stream comprising condensed water and a stream comprising alkene, unconverted alkane, carbon dioxide, unconverted oxygen, carbon monoxide and optionally alkyne.

In water removal step (b), the temperature may be of from 10 to 150° C., for example of from 20 to 80° C. Suitably, in said step (b), the temperature is at least 10° C. or at least 20° C. or at least 30° C. Further suitably, in said step (b), the temperature is at most 150° C. or at most 120° C. or at most 100° C. or at most 80° C. or at most 60° C.

Still further, in water removal step (b), typical pressures are 0.1-30 or 0.1-20 bara (i.e. "bar absolute").

Further, preferably, said pressure is of from 0.1 to 15 bara, more preferably of from 1 to 8 bara, most preferably of from 3 to 8 bara.

In a case wherein the stream as fed to water removal step (b) additionally comprises a carboxylic acid, for example acetic acid and/or acrylic acid, said carboxylic acid is removed in water removal step (b) together with the water from said stream, suitably together with the water as condensed from said stream. During or after water removal step (b), additional water may be added to facilitate the removal of any carboxylic acid.

Step (c) of the process of the present invention comprises removing unconverted oxygen, carbon monoxide and optionally alkyne from a stream comprising alkene, unconverted alkane, carbon dioxide, unconverted oxygen, carbon monoxide and optionally an alkyne, preferably the stream resulting from step (b), in particular from at least part of the stream comprising alkene, unconverted alkane, carbon dioxide, unconverted oxygen, carbon monoxide and optionally an alkyne resulting from step (b), wherein carbon monoxide and optionally alkyne are oxidized into carbon dioxide, resulting in a stream comprising alkene, unconverted alkane and carbon dioxide. Like with any oxidation of hydrocarbons, such as alkynes, water is produced.

In oxygen and carbon monoxide removal step (c), the temperature may vary within wide ranges and is generally of from 50 to 500° C., for example of from 100 to 400° C. Preferably, in said step (c), the temperature is in the range of from 100 to 400° C., more preferably 150 to 300° C., most preferably 200 to 260° C. In said step (c), the temperature may be at least 50° C. or at least 100° C. or at least higher than 100° C. or at least 110° C. or at least higher than 110° C. or at least 120° C. or at least higher than 120° C. or at least 130° C. or at least higher than 130° C. or at least 140° C. or at least higher than 140° C. or at least 150° C. or at least higher than 150° C. or at least 160° C. or at least higher than 160° C. or at least 170° C. or at least higher than 170° C. or at least 180° C. or at least higher than 180° C. or at least 190° C. or at least higher than 190° C. or at least 200° C. or at least higher than 200° C. or at least 210° C. or at least 220° C. or at least 230° C. or at least 240° C. Further, in said step (c), the temperature may be at most 500° C. or at most 400° C. or at most 350° C. or at most 340° C. or at most 330° C. or at most 320° C. or at most 310° C. or at most 300° C. or at most 290° C. or at most 280° C. or at most 270° C. or at most 260° C. or at most 250° C.

Still further, in oxygen and carbon monoxide removal step (c), typical pressures are 0.1-30 or 0.1-20 bara (i.e. "bar absolute"). Further, preferably, said pressure is of from 0.1 to 15 bara, more preferably of from 1 to 8 bara, most preferably of from 2 to 7 bara.

Further, in the process of the present invention, additional oxygen may be fed to oxygen and carbon monoxide removal step (c). Such additional oxygen is added in addition to the oxygen from the stream comprising alkene, unconverted alkane, carbon dioxide, unconverted oxygen, carbon monoxide and optionally an alkyne that is fed to said step (c). Such additional oxygen may be needed in a case where the latter stream does not contain sufficient unconverted oxygen to oxidize all of the carbon monoxide and any alkyne from the same stream into carbon dioxide. Such additional oxygen may be added either directly or indirectly to oxygen and carbon monoxide removal step (c), in particular at any point before and/or during oxygen and carbon monoxide removal step (c).

In oxygen and carbon monoxide removal step (c), oxygen and optionally alkyne are removed from the stream comprising alkene, unconverted alkane, carbon dioxide, unconverted oxygen, carbon monoxide and optionally an alkyne by oxidation of carbon monoxide and any alkyne into carbon dioxide. That is to say, unconverted oxygen from the latter stream is used to oxidize carbon monoxide and any alkyne into carbon dioxide. As mentioned above, additional oxygen may be fed to fully convert all carbon monoxide and alkyne (if any) into carbon dioxide. Such oxidation may also be referred to as combustion. Thus, said step (c) results in a stream comprising alkene, unconverted alkane and carbon dioxide.

It is also envisaged that in a case where an alkyne (for example acetylene) is produced in ODH alkane ODH step (a), such alkyne may be removed before oxygen and carbon monoxide removal step (c), for example between steps (b) and (c), and in particular by means of hydrogenation of the alkyne into the corresponding alkene.

Suitably, in oxygen and carbon monoxide removal step (c), oxygen may be removed to such an extent that the stream resulting from said step (c) comprises no oxygen or a residual amount of oxygen which is at most 10,000 parts per million by volume (ppmv) or at most 1,000 ppmv or at most 500 ppmv or at most 100 ppmv or at most 50 ppmv or at most 10 ppmv or at most 2 ppmv or at most 1 ppmv, based on the total volume of the stream resulting from said step (c). Further, suitably, in oxygen and carbon monoxide removal step (c), carbon monoxide and any alkyne may be removed to such an extent that the stream resulting from said step (c) comprises no carbon monoxide and alkyne or a residual amount of carbon monoxide and alkyne which is at most 15 vol. % or at most 10 vol. % or at most 5 vol. % or at most 1 vol. % or at most 500 parts per million by volume (ppmv) or at most 100 ppmv or at most 50 ppmv or at most 10 ppmv or at most 2 ppmv or at most 1 ppmv, based on the total volume of the stream resulting from said step (c).

Oxygen and carbon monoxide removal step (c) may be carried out in the presence of a catalyst, suitably an oxidation catalyst. Suitably, said oxidation catalyst catalyzes the oxidation of carbon monoxide and any alkyne into carbon dioxide. In particular, suitably, said oxidation catalyst catalyzes the conversion of carbon monoxide and any alkyne and oxygen into carbon dioxide by means of oxidation of carbon monoxide and any alkyne into carbon dioxide.

In oxygen and carbon monoxide removal step (c), any oxidation catalyst that catalyzes the oxidation of carbon monoxide into carbon dioxide may be used. For example, one of the carbon monoxide oxidation catalysts as described in EP499402A1, U.S. Pat. No. 4,956,330, EP306945A1, EP421169A1, U.S. Pat. Nos. 5,157,204 and 5,446,232 may be used in said step (c), the disclosures of which are herein incorporated by reference. Preferably, said catalyst also catalyzes the oxidation of any alkyne, for example acetylene, into carbon dioxide.

Preferably, the above-mentioned oxidation catalyst that may be used in oxygen and carbon monoxide removal step (c) comprises a transition metal. More preferably, said catalyst comprises one or more metals selected from the group consisting of nickel (Ni), copper (Cu), zinc (Zn), palladium (Pd), silver (Ag), platinum (Pt), gold (Au), iron (Fe), manganese (Mn), cerium (Ce), tin (Sn), ruthenium (Ru) and chromium (Cr), more preferably one or more metals selected from the group consisting of nickel, copper, zinc, silver, platinum and ruthenium, more preferably one or more metals selected from the group consisting of nickel, copper, zinc, platinum and ruthenium, more preferably one or more metals selected from the group consisting of nickel, copper, zinc and silver, even more preferably one or more metals selected from the group consisting of nickel, copper and zinc. Most preferably, said catalyst comprises copper and/or platinum. Suitably, said catalyst comprises copper or platinum, more suitably copper. For example, said catalyst may comprise copper and zinc. In particular, said catalyst may be a metal oxide catalyst, which may be a partially reduced metal oxide catalyst, wherein the metal(s) is (are) as described above, for example a catalyst comprising copper oxide and optionally zinc oxide. The catalyst may be a supported catalyst, wherein one or more of said metals are carried by a support, or an unsupported catalyst. In case the catalyst is a supported catalyst, the support may be any support, for example alumina, titania, silica, zirconia or silicon carbide, suitably alumina. Further, the supported catalyst may be shaped into any shape, including tablets and extrudates, or coated on a substrate.

Further, in the present invention, the above-mentioned oxidation catalyst that may be used in oxygen and carbon monoxide removal step (c) may comprise one or more metals selected from the group consisting of palladium, silver, platinum, gold, copper and ruthenium, or one or more metals selected from the group consisting of palladium, silver, platinum and gold, or platinum.

As described above, in the process of WO2010115108, the removal of oxygen and any carbon monoxide and acetylene (an alkyne) takes place before water removal. This is different from the process of the present invention wherein only after removal of water from an alkane oxidative dehydrogenation (ODH) effluent comprising alkene, unconverted alkane, water, carbon dioxide, unconverted oxygen, carbon monoxide and optionally an alkyne, removal of unconverted oxygen, carbon monoxide and optionally alkyne from that stream is performed by oxidation of carbon monoxide and any alkyne into carbon dioxide.

Such change in order of steps, that is to say the water removal step and the oxygen and carbon monoxide removal step, results in the following advantages for the present invention.

Since in the process of the present invention, water has already been removed in step (b) before oxygen and carbon monoxide removal step (c) is performed, in the latter step a stream having a relatively small volume may be processed. For example, this may advantageously result in that a reactor used in said step (c) may be relatively small.

Further, in the process of WO2010115108, during the step of removing oxygen and any carbon monoxide and acetylene which is performed before water removal, water is still present. During said step, condensation of water should be prevented in order to avoid wetting of the oxygen removal catalyst. This implies that the oxygen removal step in the process of WO2010115108 has to be carried out at a relatively high temperature.

As a consequence of such high temperature, a water gas shift reaction may take place during the oxygen removal step in the process of WO2010115108, which is undesired. A water gas shift reaction involves the reaction of carbon monoxide with water into hydrogen ($H_2$) and carbon dioxide, which may take place at a temperature of 200° C. or higher. However, advantageously, in step (b) of the process of the present invention water may be removed at a relatively low temperature (e.g. of from 10 to 150° C.), as a consequence of which advantageously no or substantially no water gas shift reaction could take place during said step (b). Since in said step (b) the water gas shift reaction may be minimized, no or substantially less hydrogen may be formed which hydrogen could otherwise undesirably reduce the desired alkene product to alkane.

Still further, in oxygen and carbon monoxide removal step (c) of the process of the present invention, carbon monoxide and any alkyne (for example acetylene) may be removed by combustion into carbon dioxide, while still advantageously minimizing the undesired oxidation of unconverted alkane and alkene product.

Still further, in said step (c), water and other oxygenate compounds originating from water removal step (b) may be present without preventing said removal of carbon monoxide and optionally alkyne. Such other oxygenate compounds may include carboxylic acids (for example acetic acid), aldehydes (for example acetaldehyde) and ketones (for example acetone). Said water and other oxygenate compounds may for example be present in an amount which ranges of from 10 parts per million by volume (ppmv) to 2 vol. %, suitably of from 50 ppmv to 1 vol. %, more suitably of from 100 ppmv to 1,000 ppmv. Preferably, said other oxygenate compounds, especially carboxylic acids, may advantageously also be removed by conversion, in addition to the removal of carbon monoxide and optionally alkyne by combustion into carbon dioxide.

Preferably, in the stream comprising alkene, unconverted alkane, carbon dioxide, unconverted oxygen, carbon monoxide and optionally alkyne sent to step (c), substantially no carboxylic acid is present or carboxylic acid is present in an amount of at most 2 vol. % or at most 1 vol. % or at most 1,000 ppmv or at most 500 ppmv or at most 100 ppmv or at most 50 ppmv or at most 20 or at most 10 ppmv.

From the above it appears that with the present invention a process may be provided wherein oxygen, carbon monoxide and optionally alkyne are removed from alkane ODH effluent, which is technically advantageous, efficient and affordable. Such technically advantageous process would preferably result in a relatively low energy demand and/or relatively low capital expenditure.

In one embodiment of the present process, step (c) of the present process may coincide with the conversion of the alkene into a product. In particular, step (c) of the present process may coincide with the oxidation of the alkene into a product other than carbon monoxide and carbon dioxide, for example the oxidation of ethylene into ethylene oxide. Thus, in the latter case, (i) oxidation of carbon monoxide, as produced in alkane ODH step (a), into carbon dioxide and (ii) oxidation of ethylene into ethylene oxide may proceed simultaneously, for example using a silver containing catalyst which is suitable for the production of ethylene oxide from ethylene using oxygen. In another embodiment of the present process, in step (c) of the present process, the alkene is substantially not converted into a product other than carbon monoxide or carbon dioxide, resulting in a stream comprising alkene, unconverted alkane and carbon dioxide which stream contains substantially no alkene product other than carbon monoxide and carbon dioxide. In particular, in the latter embodiment, step (c) of the present process results in a stream comprising alkene, unconverted alkane and carbon dioxide which stream contains substantially no ethylene oxide and substantially no vinyl acetate, suitably a stream comprising alkene, unconverted alkane and carbon dioxide which stream contains substantially no ethylene oxide.

In some cases, in oxygen and carbon monoxide removal step (c), it may not be possible or desired to completely remove oxygen, carbon monoxide and optionally alkyne by oxidation of carbon monoxide and optionally alkyne into carbon dioxide, using unconverted oxygen and any additional oxygen as described above. If that is the case and if it is desired to remove any remaining amount of oxygen and/or carbon monoxide and/or alkyne, after said oxidation, a further removal treatment may be carried out as part of oxygen and carbon monoxide removal step (c). Such further removal treatment may comprise passing the stream though a guard bed comprising a sorbent (adsorbent and/or absorbent) which is capable of selectively sorbing any remaining oxygen, carbon monoxide and alkyne.

Step (d) of the process of the present invention is optional and comprises removing carbon dioxide from a stream comprising alkene, unconverted alkane and carbon dioxide, preferably the stream resulting from step (c), in particular from at least part of the stream comprising alkene, unconverted alkane and carbon dioxide resulting from step (c), resulting in a stream comprising alkene and unconverted alkane.

In carbon dioxide removal step (d), carbon dioxide may be removed by any one of well-known methods. A suitable carbon dioxide removal agent that may be fed to said step (d) may be an aqueous solution of a base, for example sodium hydroxide and/or an amine. After such carbon dioxide removal, the stream from which carbon dioxide is removed may be dried to remove any residual water from the stream before it is fed to the next step. Contacting an aqueous solution of an amine with a carbon dioxide containing stream is preferred in a case where the carbon dioxide amount is relatively high, for example in the case of an alkane ODH effluent. Contacting an aqueous solution of sodium hydroxide with a carbon dioxide containing stream is preferred in a case where the carbon dioxide amount is relatively low, for example in the case of an alkane ODH effluent that was treated with an aqueous solution of an amine and which still contains some residual carbon dioxide.

It is envisaged in the present invention that in carbon dioxide removal step (d) of the present process, a stream comprising alkene, unconverted alkane and carbon dioxide, preferably the stream resulting from oxygen and carbon monoxide removal step (c) of the present process, in particular at least part of the stream comprising alkene, unconverted alkane and carbon dioxide resulting from said step (c), may be combined with a carbon dioxide containing stream originating from another process.

In a case wherein the stream resulting from carbon dioxide removal step (d) also comprises water originating from the carbon dioxide removal agent, such stream comprising alkene, unconverted alkane and water may be dried resulting in a stream comprising alkene and unconverted alkane that may be fed to step (e) of the present process.

Step (e) of the process of the present invention is optional and comprises separating a stream comprising alkene and unconverted alkane, preferably the stream resulting from step (d), in particular at least part of the stream comprising alkene and unconverted alkane resulting from step (d), into a stream comprising alkene and a stream comprising unconverted alkane. The desired alkene (for example ethylene) and unconverted alkane (for example ethane) may be separated from each other in any way, for example by means of distillation, absorption or adsorption. For example, it is known to separate ethane from ethylene, by means of cryogenic distillation in so-called "C2 splitter" columns. In such cryogenic distillation, a relatively high pressure and a relatively low (cryogenic) temperature are applied to effect the separation of ethane from ethylene.

Further, in step (e) of the process of the present invention the stream to be separated may be a stream which comprises components having a boiling point lower than alkenes and alkanes having 2 or more carbon atoms. Such components having a lower boiling point may comprise any carbon monoxide that is not removed in step (c) of the present process; any methane from the feed to step (a) of the present process; nitrogen from any air fed to step (a) of the present process to provide oxygen as oxidizing agent; any argon; and so on. In such case, said components having a lower boiling point may first be separated from the other components, comprising alkene and unconverted alkane having 2 or more carbon atoms, after which alkene having 2 or more carbon atoms may be separated from unconverted alkane having 2 or more carbon atoms. Alternatively, said components having a lower boiling point may be separated together with alkene having 2 or more carbon atoms from unconverted alkane having 2 or more carbon atoms, after which alkene having 2 or more carbon atoms may be separated from said components having a lower boiling point. All of said separations may be performed by cryogenic distillation.

Step (f) of the process of the present invention is optional and comprises recycling unconverted alkane from a stream comprising unconverted alkane, preferably the stream comprising unconverted alkane resulting from step (e), in particular from at least part of the stream comprising unconverted alkane resulting from step (e), to step (a).

Figure 1:
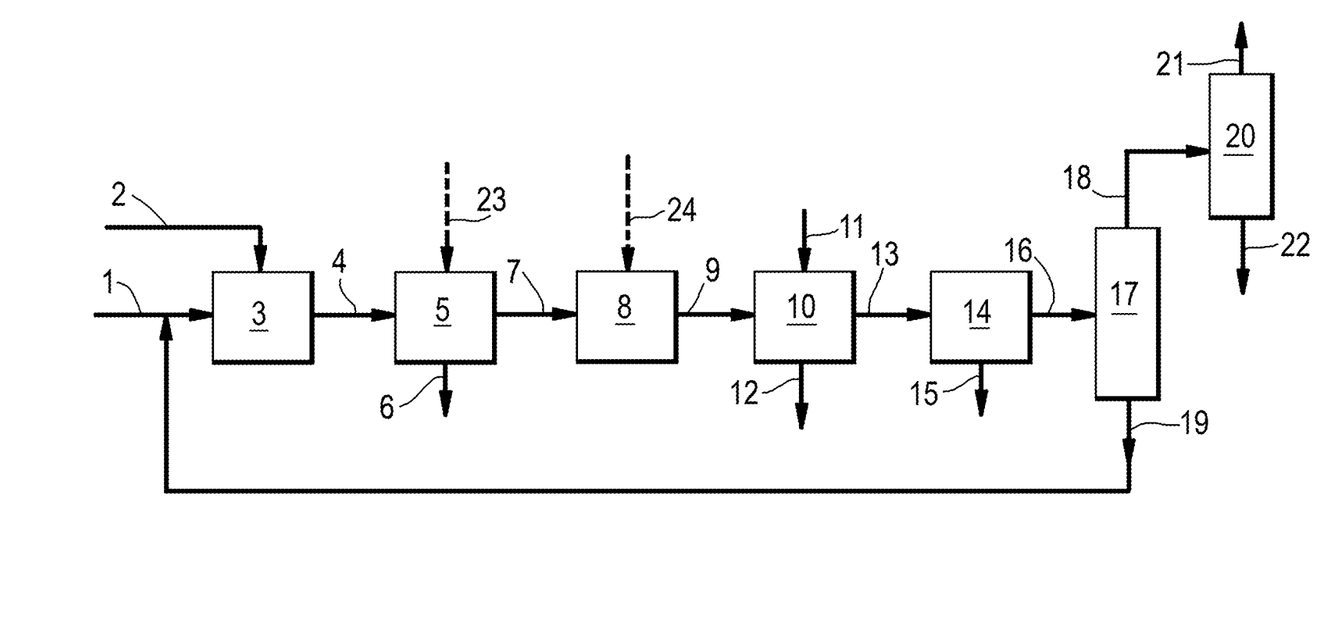
FIG. 1 depicts an embodiment of the process of the present invention wherein oxygen, carbon monoxide and alkyne are removed after removing water from the stream resulting from the alkane oxidative dehydrogenation (ODH) step.

The process of the present invention is further illustrated by FIG. 1.

In FIG. 1, stream 1 comprising ethane and stream 2 comprising oxygen are fed to oxidative dehydrogenation (ODH) unit 3 containing an ODH catalyst comprising a mixed metal oxide and operating under ODH conditions, wherein ethane is converted into ethylene in accordance with the above-described step (a) of the process of the present invention. Product stream 4 coming from ODH unit 3 comprises water, ethane, ethylene, oxygen, carbon monoxide, acetylene, carbon dioxide and any acetic acid. Said stream 4 is fed to water condensation unit 5. In water condensation unit 5, water and any acetic acid are removed by condensation via stream 6 in accordance with the above-described step (b) of the process of the present invention. Optionally, additional water is fed to water removal unit 5 via stream 23. Stream 7 coming from water condensation unit 5, which comprises ethane, ethylene, oxygen, carbon monoxide, acetylene and carbon dioxide, is fed to oxygen and carbon monoxide removal unit 8. In oxygen and carbon monoxide removal unit 8, oxygen, acetylene and carbon monoxide are removed in accordance with the above-described step (c) of the process of the present invention, wherein carbon monoxide and any alkyne (e.g. acetylene) are oxidized into carbon dioxide. Optionally, additional oxygen is fed to oxygen and carbon monoxide removal unit 8 via stream 24. Product stream 9 coming from oxygen and carbon monoxide removal unit 8 comprises ethane, ethylene and carbon dioxide. Said stream 9 is fed to carbon dioxide removal unit 10. Carbon dioxide removal agent is fed to carbon dioxide removal unit 10 via stream 11. Said carbon dioxide removal agent is an aqueous solution of a base, for example sodium hydroxide and/or an amine. Carbon dioxide is removed via aqueous stream 12 in accordance with the above-described step (d) of the process of the present invention. Stream 13 coming from carbon dioxide removal unit 10, which comprises ethane, ethylene and water, is fed to drying unit 14. In drying unit 14, water is removed via stream 15. Stream 16 coming from drying unit 14, which comprises ethane and ethylene, is fed to separation unit 17 wherein said stream is separated in accordance with the above-described step (e) of the process of the present invention. In separation unit 17, said stream 16 is separated into a top stream 18 comprising ethylene and a bottom stream 19 comprising ethane which is recycled to ODH unit 3 in accordance with the above-described step (f) of the process of the present invention. In a case wherein said top stream 18 additionally comprises components having a boiling point lower than ethylene and ethane, said stream 18 is fed to separation unit 20. In separation unit 20, stream 18 comprising ethylene and components having such lower boiling point is separated into a top stream 21 comprising components having a boiling point lower than ethylene and ethane and a bottom stream 22 comprising ethylene.

EXAMPLE 1

In the experiments of Example 1, a gas stream having the composition as described in Table 1 below was fed to the top of a vertically oriented, tubular, quartz reactor and then sent downwardly through the catalyst bed to the bottom of the reactor. The reactor had an inner diameter of 4 mm and a length of 480 mm. The reactor was situated within a temperature controlled radiation oven. The gas hourly space velocity was 10,666 Nl/liter catalyst/hour. "Nl" stands for "normal litre" as measured at standard temperature and pressure, namely 32° F. (0° C.) and 1 bara (100 kPa). The pressure in the reactor was 4.1 bara.

TABLE 1

|  | Nl/hour | Vol. % |
| --- | --- | --- |
| Oxygen ($O_2$) | 0.06 | 1.13 |
| Nitrogen ($N_2$) | 5.224 | 98.01 |
| Carbon monoxide (CO) | 0.0135 | 0.253 |
| Acetylene ($C_2H_2$) | 0.0081 | 0.152 |
| Ethylene ($C_2H_4$) | 0.0081 | 0.152 |
| Ethane ($C_2H_6$) | 0.0081 | 0.152 |
| Carbon dioxide ($CO_2$) | 0.0081 | 0.152 |
| Total | 5.33 | 100 |

The isothermal temperature zone of the reactor was loaded with a catalyst which comprised 41 wt. % of CuO, 31 wt. % of ZnO and 28 wt. % of alumina. The catalyst was in the form of pellets having a diameter of 5.2 mm and a length of 3.0 mm. Further, the catalyst had a bulk density of 1.380 kg/m$^3$ and a crush strength (axial) of 220 kgf. The catalyst had a size of 40-80 mesh. The amount of catalyst used was 0.375 gram (0.502 ml). The catalyst bed height in the reactor was 4 cm.

The reactor was heated: the catalyst temperature is shown in Table 2 below. Further, the experimental results are shown in Table 2 with respect to the percentage of acetylene ($C_2H_2$) from the feed that was converted to carbon dioxide ($CO_2$). The percentage of carbon monoxide (CO) from the feed that was converted to $CO_2$ is also shown in Table 2. Further, Table 2 shows the percentage of the total of ethylene ($C_2H_4$) and ethane ($C_2H_6$) from the feed that was converted to $CO_2$.

TABLE 2

| Exp. | Temp. (° C.) | $C_2H_2$ to $CO_2$ (%) | CO to $CO_2$ (%) | $C_2H_4 + C_2H_6$ to $CO_2$ (%) |
| --- | --- | --- | --- | --- |
| 1 | 225 | 97 | 25 | <1 |
| 2 | 233 | 100 | 100 | <3 |

From the experimental results in Table 2 above, it appears that both carbon monoxide and acetylene may advantageously be removed by combustion into carbon dioxide, in the presence of other components such as ethylene and ethane, while advantageously minimizing the undesired oxidation of said ethylene and ethane.

EXAMPLE 2

In the experiments of Example 2, a gas stream having the composition as described in Table 3 below was fed to the top of a vertically oriented, tubular, stainless steel reactor and then sent downwardly through the catalyst bed to the bottom of the reactor. The reactor had an inner diameter of 7.05 mm and a length of 715 mm. The reactor was situated within a temperature controlled radiation oven. The gas hourly space velocity was 2,399 Nl/liter catalyst/hour. The pressure in the reactor was 2.6 bara.

TABLE 3

|  | Nl/hour | Vol. % |
| --- | --- | --- |
| Oxygen ($O_2$) | 0.082 | 1.01 |
| Nitrogen ($N_2$) | 1.558 | 19.148 |
| Carbon monoxide (CO) | 0.287 | 3.527 |
| Acetylene ($C_2H_2$) | 0.00179 | 0.022 |
| Ethylene ($C_2H_4$) | 2.827 | 34.745 |

TABLE 3-continued

|  | Nl/hour | Vol. % |
|---|---|---|
| Ethane ($C_2H_6$) | 3.091 | 37.989 |
| Carbon dioxide ($CO_2$) | 0.142 | 1.745 |
| Water ($H_2O$) | 0.147 | 1.807 |
| Acetic acid ($C_2H_4O_2$) | 0.00072 | 0.0088 |
| Total | 8.136 | 100 |

The isothermal temperature zone of the reactor was loaded with a catalyst which comprised 41 wt. % of CuO, 31 wt. % of ZnO and 28 wt. % of alumina. The catalyst was in the form of pellets having a diameter of 5.2 mm and a length of 3.0 mm. Further, the catalyst had a bulk density of 1.091 kg/m³ and a crush strength (axial) of 220 kgf. The catalyst had a size of 40-80 mesh. The amount of catalyst used was 3.701 gram (3.392 ml). The catalyst bed height in the reactor was 8.5 cm.

The reactor was heated: the catalyst temperature is shown in Table 4 below. Further, the experimental results are shown in Table 4 with respect to the percentage of acetylene ($C_2H_2$) from the feed that was converted to carbon dioxide ($CO_2$). The percentage of carbon monoxide (CO) from the feed that was converted to $CO_2$ is also shown in Table 4. Further, Table 4 shows the conversion of oxygen ($O_2$). Still further, Table 4 shows the percentage of the total of ethylene ($C_2H_4$) and ethane ($C_2H_6$) from the feed that was converted to $CO_2$.

TABLE 4

| Exp. | Temp. (° C.) | $C_2H_2$ to $CO_2$ (%) | $O_2$ conversion (%) | CO to $CO_2$ (%) | $C_2H_4 + C_2H_6$ to $CO_2$ (%) |
|---|---|---|---|---|---|
| 3 | 166 | 100 | 28 | 9 | <1 |
| 4 | 171 | 100 | 33.7 | 12.4 | <1 |
| 5 | 176 | 100 | 40.7 | 13.9 | <1 |
| 6 | 199 | 100 | 96.5 | 41.5 | <1 |
| 7 | 203 | 100 | 100 | 56.2 | <1 |
| 8 | 216 | 100 | 100 | 57.2 | <1 |
| 9 | 227 | 100 | 100 | 52.5 | <1 |
| 10 | 247 | 100 | 100 | 53.0 | <1 |

From the experimental results in Table 4 above, it appears that both carbon monoxide and acetylene may advantageously be removed by combustion into carbon dioxide, in the presence of other components such as ethylene, ethane, water and acetic acid, while advantageously minimizing the undesired oxidation of said ethylene and ethane and at the same time removing oxygen.

Further, for Experiments 7 and 8 from Table 4 above, the conversion of acetic acid ($C_2H_4O_2$) was also determined (by ion chromatography), which conversion was 77.8% (Exp. 7, at 203° C.) and 51.4% (Exp. 8, at 216° C.), respectively. From that it appears that not only carbon monoxide and acetylene may advantageously be removed in the presence of acetic acid by combustion into carbon dioxide, the latter acetic acid itself is also advantageously converted.

EXAMPLE 3

The experiment of Example 3 was carried out in the same way as the experiments of Example 2, except that no water and no acetic acid were present in the gas stream fed to the reactor (see composition as described in Table 5 below), a different temperature was applied (see Table 6 below) and a different GHSV was used, namely 2,407 Nl/liter catalyst/hour.

TABLE 5

|  | Nl/hour | Vol. % |
|---|---|---|
| Oxygen ($O_2$) | 0.085 | 1.041 |
| Nitrogen ($N_2$) | 1.595 | 19.528 |
| Carbon monoxide (CO) | 0.286 | 3.502 |
| Acetylene ($C_2H_2$) | 0.00162 | 0.0198 |
| Ethylene ($C_2H_4$) | 2.827 | 34.612 |
| Ethane ($C_2H_6$) | 3.230 | 39.546 |
| Carbon dioxide ($CO_2$) | 0.143 | 1.751 |
| Total | 8.168 | 100 |

TABLE 6

| Exp. | Temp. (° C.) | $C_2H_2$ to $CO_2$ (%) | $O_2$ conversion (%) | CO to $CO_2$ (%) | $C_2H_4 + C_2H_6$ to $CO_2$ (%) |
|---|---|---|---|---|---|
| 11 | 206 | 100 | 100 | 50.4 | <1 |

From the experimental results in Table 6 above, it appears that both carbon monoxide and acetylene may advantageously be removed by combustion into carbon dioxide, in the presence of other components such as ethylene and ethane, while advantageously minimizing the undesired oxidation of said ethylene and ethane and at the same time removing oxygen.

That which is claimed is:

1. A process for producing ethylene by ethane oxidative dehydrogenation, comprising:
   (a) subjecting a stream comprising ethane to oxidative dehydrogenation conditions, comprising contacting ethane with oxygen in the presence of a catalyst comprising a mixed metal oxide, resulting in a stream comprising ethylene, unconverted ethane, water, carbon dioxide, unconverted oxygen, carbon monoxide and acetylene;
   (b) removing water from at least part of the stream comprising ethylene, unconverted ethane, water, carbon dioxide, unconverted oxygen, carbon monoxide and acetylene resulting from step (a), resulting in a stream comprising ethylene, unconverted ethane, carbon dioxide, unconverted oxygen, carbon monoxide and acetylene;
   (c) removing unconverted oxygen, carbon monoxide and acetylene from at least part of the stream comprising ethylene, unconverted ethane, carbon dioxide, unconverted oxygen, carbon monoxide and acetylene resulting from step (b), resulting in a stream comprising ethylene, unconverted ethane and carbon dioxide, wherein the removing unconverted oxygen, carbon monoxide and acetylene is carried out by oxidizing carbon monoxide and acetylene with unconverted oxygen into carbon dioxide;
   (d) removing carbon dioxide from at least part of the stream comprising ethylene, unconverted ethane and carbon dioxide resulting from step (c), resulting in a stream comprising ethylene and unconverted ethane;
   (e) separating at least part of the stream comprising ethylene and unconverted ethane resulting from step (d), into a stream comprising ethylene and a stream comprising unconverted ethane;
   (f) optionally recycling ethane from at least part of the stream comprising unconverted ethane resulting from step (e), to step (a).

2. The process according to claim 1, wherein a temperature in step (c) is in a range of from 100 to 400° C.

3. The process according to claim 1, wherein a temperature in step (c) is at least 50° C.

4. The process according to claim 1, wherein a temperature in step (c) is at most 500° C.

5. The process according to claim 1, wherein additional oxygen is fed to step (c).

6. The process according to claim 1, wherein step (c) is performed in presence of an oxidation catalyst comprising a transition metal.

7. The process according to claim 6, wherein the oxidation catalyst comprises one or more metals selected from the group consisting of nickel, copper, zinc, palladium, silver, platinum, gold, iron, manganese, cerium, tin, ruthenium and chromium.

8. The process according to claim 6, wherein the oxidation catalyst comprises copper and/or platinum.

* * * * *